United States Patent [19]
Behre et al.

[11] Patent Number: 6,133,480
[45] Date of Patent: Oct. 17, 2000

[54] PREPARATION OF N-PHENYL-1-NAPHTHYLAMINE

[75] Inventors: Horst Behre, Odenthal; Helmut Fiege, Leverkusen; Wolfgang Eymann, Köln; Frank Arndt, Krefeld; Rudolf Wiemers, Meerbusch; Alexander Klausener, Pulheim, all of Germany

[73] Assignee: Bayer Aktiengesellschaft, Leverkusen, Germany

[21] Appl. No.: 09/209,401

[22] Filed: Dec. 10, 1998

[30] Foreign Application Priority Data

Dec. 17, 1997 [DE] Germany .......................... 197 56 145

[51] Int. Cl.⁷ .................................................. C07C 211/00
[52] U.S. Cl. .................................................. 564/429
[58] Field of Search ............................... 564/429

[56] References Cited

U.S. PATENT DOCUMENTS 4,100,195 7/1978 Fischler .
5,658,866 8/1997 Yoshida et al. .

FOREIGN PATENT DOCUMENTS 241853 11/1911 Germany .

OTHER PUBLICATIONS

Ullmanns Encyclopaedia of Industrial Chemistry, 4th ed., vol. 17, (month unavailable) 1979, p. 107.

H.E. Fierz–David and L. Blangley, Farbenchemie, 8th ed., p. 171, (month unavailable) 1952.

J. Prakt Chem 89, 1 (month unavailable) 1914.

CA 95:80324 (1981).

Chemicky Prümysl, pp. 300–306, 1981 (month available), Jan Uhlár et al. Priprava difenylaminu z amillnu katalýzy zlücenin o premenlivom atomárnom pomere fluör k bóru.

Primary Examiner—Paul J. Killos
Attorney, Agent, or Firm—Joseph C. Gil; Lyndanne M. Whalen; Diderico Van Eyl

[57] ABSTRACT

N-Phenyl-1-naphthylamine can be prepared by reaction of aniline and 1-naphthylamine in the liquid phase at 100–400° C. under normal pressure, a catalyst mixture comprising boron and fluorine being employed. Such catalyst mixtures can be obtained, for example, by reaction of hydrogen fluoride, boric acid and aniline and/or 1-naphthylamine. The catalyst is recovered and can be employed again. The reaction can be carried out discontinuously or continuously.

12 Claims, No Drawings

PREPARATION OF N-PHENYL-1-NAPHTHYLAMINE

The present invention relates to a process for the preparation of N-phenyl-1-naphthylamine (phenyl-α-naphthylamine) of the formula (I)

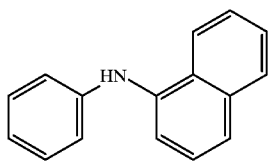

(I)

by reaction of aniline with 1-naphthylamine, wherein the reaction is carried out in the presence of a catalyst comprising boron and fluorine, in the condensed phase and under normal ambient pressure.

N-Phenyl-1-naphthylamine is employed, for example, as an anti-ageing agent or antioxidant for rubber and for mineral oil products (Ullrnanns Encyklopädie der technician Chemie [Ullmann's Encyclopaedia of Industrial Chemistry], 4th edition, vol. 17, p. 107, Verlag Chemie, Weinheim 1979). Further possible uses are in the field of dyestuffs. Thus, for example, the dyestuff Victoria blue, a diphenyl-naphthylmethane derivative, is obtained starting from N-phenyl-1-naphthylamine (H. E. Fierz-David and L. Blangley, Farbenchemie, 8th ed., p. 171, Springer-Verlag, Vienna 1952). Derivatives of N-phenyl-1-naphthylamine which are prepared either from this compound itself or analogously to this compound are also of interest as components of lubricants (EP 716 141).

Various processes for the preparation of N-phenyl-1-naphlhylamine have been described in the literature. Thus, according to BIOS Final Report 986, II, p. 363, N-phenyl-1-naphthylamine is obtained by reaction of aniline and 1-naphthylamine at temperatures of 230–250° C. in the presence of catalytic amounts of p-toluenesulfo acid. Yields of up to 91% of the theoretical yield are achieved here. A disadvantage of this process is that the catalyst evidently cannot be re-used, which must be evaluated as unsatisfactory from economic and ecological aspects. According to H. E. Fierz-David and L. Blangley, Farbenchemie, 8th ed., p. 171, ,pringer-Verlag, Vienna 1952, N-phenyl-1-naphthylamine is obtained in yields of 86–91% of the theoretical yield by reaction of aniline and 1-naphthylamine at temperatures of 195–215° C., sulfanilic acid being used as the catalyst. As in the process mentioned above, there is also no recovery of the catalyst here, so that the economic and ecological disadvantages are the same. According to a procedure described in DE-PS 241 853 and in J. Prakt. Chem. 89, I (1914), N-phenyl-1-naphthylamine is obtained by reaction of aniline and 1-naphthylamine at temperatures of 225–250° C. in the presence of catalytic amounts of iodine. In this variant also, the catalyst is not re-used, so that there are also economic and ecological disadvantages here. Furthermore, the reaction yields described are significantly lower than in the abovementioned process. According to J. Prakt. Chem. 89, I (1914), N-phenyl-1-naphthylamine car, also be obtained by reaction of 1 -naphthol with aniline at temperatures between 180 and 200° C., likewise in the presence of catalytic amounts of iodine. However, the yields reach only 35–40% of the theoretical yield, which makes this variant seem significantly less favourable than those described above.

All the processes mentioned have the common feature that in the course thereof greater or lesser amounts of undesirable by-products, such as, for example, diphenylamine, N-phenyl-2-naphthylamine and 2-naphthylamine, are formed. The compounds mentioned last, N-phenyl-2-naphthylamine and 2-naphthylamine, above all can be formed in principle by isomerization of the N-phenyl-1-naphthylamine already formed or of unreacted 1-naphthylamine, in particular depending on the reaction conditions applied and the catalyst used. Apart from the fact that the formation of such undesirable by-products causes a considerable impairment to the profitability of the particular preparation process, because of the associated losses of material and the increased expenditure on separation which becomes necessary to isolate pure N-phenyl-1-naphthylamine, it should furthermore be take-n into account that 2-naphthylamine in particular has highly toxic properties and its formation is therefore to be ruled out as far as possible.

There was thus the object of discovering an economic process for the highly selective preparation of N-phenyl-1-naphthylamine in which the formation of undesirable by-products, but above all the formation of 2-naphthylamine, is; largely ruled out and which allows recycling of the catalyst used.

It has been found, surprisingly, that N-phenyl-1-naphthylamine can be obtained in high yields and excellent selectivities if aniline and 1-naphthylamine are reacted with one another in the presence of a catalyst containing hydrogen fluoride, boric acid and aniline and/or 1-naphthylamine. The observation that the catalyst employed according to the invention can be recovered by aqueous extraction from the reacted reaction mixture in a simple manner, that is to say without purification and working up, was furthermore surprising. The catalyst recovered in such a manner can be recycled into the reaction without this leading to unacceptable adverse consequences for the yield and selectivity. In view of the prior art described above, these favourable results were not to be expected. Rather, the formation of relatively large amounts of undesirable by-products and a loss of the catalyst after carrying out the reaction would have to have been expected in the reaction of aniline and 1-naphthylamine.

A process has been found for the preparation of N-phenyl-1-naphthylamine by reaction of aniline and 1-naphthylamine in the liquid phase at 100–400° C. under normal ambient pressure, which is characterized in that the reaction is carried out in the presence of a catalyst mixture comprising boron and fluorine.

Catalysts which can be used for the process according to th, invention for the preparation of N-phenyl-1-naphthylamine are either freshly prepared catalyst batches or recovered amounts of catalyst which are obtained in the course of working up of reaction mixtures. In principle, it is also possible to employ mixtures of recovered and freshly prepared catalyst. In the case where freshly prepared catalyst batches are employed, the catalyst used for the process according to the invention is preferably the reaction product which is obtained by reaction of hydrogen fluoride, boric acid and aniline and/or 1-naphthylamine. This is a salt-like product of the formula

[A][B] (II), in which represents the cations $[H]^+$, $[NH_4]^+$, $[\text{phenyl-}NH_3]^+$, $[(1\text{-naphthyl})\text{-}NH_3]^+$, $[\text{phenyl-}NH_2\text{-phenyl}]^+$ or [phenyl- $NH_2$-(1-naphthyl)]$^+$, preferably the cations [H]$^+$, [$NH_4$]$^+$, [phenyl-$NH_3$]$^+$ and [(1-naphthyl)-$NH_3$]$^+$, and particularly preferably the cations [$NH_4$]$^+$ and [phenyl-$NH_3$]$^+$, and B represents anions of the type [$B(OH)_n F_{4-n}$]$^-$, in which n can assume integral values from 0 to 4, and preferably the anion [$BF_4$]$^-$.

Important individual compounds of the formula (II) are, for example, [$NH_4$]$^+$[$BF_4$]$^-$ and [phenyl-$NH_3$]$^+$[$BF_4$]$^-$.

In practice, the catalysts which are active within the reaction according to the invention, called "catalyst according to the invention" in simplified form in the following can be mixtures of various components corresponding to the general formula (II), the composition of which, however, is established according to the stoichiometric ratios and the basicities and dissociation constants of the cationic main components of water, ammonia, aniline, 1-naphthylamine and N-phenyl-1-naphthylamine which participate, as appropriate, and which in general comprise contents of the components of water, ammonia, aniline and/or 1-naphthylamine and, where appropriate, also further aromatic diamines also in non-protonated form. Under the reaction conditions for the preparation of N-phenyl-1-naphthylamine, these mixtures are present in a homogeneously dissolved form, and thus accordingly act in their entirety as a homogeneous catalyst system.

Fresh batches of the catalyst according to the invention are in general prepared using processes known to the expert. Thus, for example, it is possible to employ aqueous solutions of ammonium tetrafluoroborate as fresh catalyst. In a preferred embodiment of the process according to the invention, the preparation of fresh batches of the catalyst according to the invention is carried out in separate, spatially separated reaction vessels. For example, the catalyst according to the invention can be prepared by a procedure in which aniline and/or 1-naphthylamine, boric acid and hydrogen fluoride are reacted with one another as reaction components. Preferably, aniline, boric acid and hydrogen fluoride are reacted with one another. Freshly added aniline and/or 1-naphthylamine is preferably employed for the preparation of the catalyst according to the invention. However, it may also be advantageous to employ recovered aniline and/or 1-naphthylamine obtained during working up of reacted reaction mixtures for this purpose.

The boric acid used for the preparation of the catalyst according to the invention is preferably employed as a solid. In principle, however, it is also possible and, where appropriate, may be advantageous to employ the boric acid as a melt, as a solution or as a suspension, for example in water and/or aniline.

The hydrogen fluoride used for the preparation of the catalyst according to the invention is preferably employed as an aqueous solution. In a preferred embodiment, the hydrogen fluoride required is employed as a concentrated aqueous solution. However, other metering modes are in principle also possible, thus, for example, the introduction of gaseous or liquefied pure hydrogen fluoride.

To prepare the catalyst according to the invention, the components participating are employed in a weight ratio of aniline and/or 1-naphthylamine:boric acid:hydrogen fluoride =(100 to 2,000): (50 to 250): (50–250). Preferably, aniline, boric acid and hydrogen fluoride are employed in a weight ratio of (300 to 1,000): (100 to 150): (100 to 150). The sequence of metering of the components mentioned in principle can be chosen freely. In a preferred embodiment, aniline is first initially introduced into the reaction vessel, boric acid is then added, and finally aqueous hydrofluoric acid is metered in.

The catalyst according to the invention is in general prepared at a reaction temperature of between 0 and 250° C., preferably between 30 and 200° C., particularly preferably between 70 and 150° C.

It may be expedient to stir the mixture during the preparation of the catalyst according to the invention. In principle, however, it is also possible to dispense with additional stirring. All or some of the heat of reaction liberated in the course of the preparation of the catalyst according to the invention can be removed by external cooling. In general, the catalyst according to the invention is prepared under normal pressure. In principle, however, it is also possible to carry out the reaction under reduced or increased pressure.

The catalyst according to the invention prepared in such a manner is in general employed in the liquid form, without isolation or further purification, in the reaction for the preparation of N-phenyl-1-naphthylamine. In principle, however, it is also possible to evaporate the catalyst according to the invention to dryness, for example under reduced pressure, and to employ the solid residue obtained as a result as the catalytically active mixture in the reaction for the preparation of N-phenyl-1-naphthylamine.

The process according to the invention initially comprises the reaction of aniline with 1-naphlhylamine, which proceeds in the liquid phase within a suitable reactor in the presence of the catalyst according to the invention. Water and/or an aqueous solution of the catalyst according to the invention is added to the liquid product mixture obtained after the end of the reaction, and the mixture is separated into a predominantly aqueous and a predominantly organic liquid phase in an apparatus suitable for this purpose.

The liquid phase, which contains the largest part of the organic material and substantially comprises the reaction product N-phenyl-1-naphthylamine, unreacted starting material, that is to say aniline and 1-naphthylamine, and small amounts of by-products, is separated off and subjected to further working up. The predominantly aqueous phase comprising the largest part of the salt-like catalyst is also separated off. It can be sluiced out entirely or in part, and/or used again entirely or in part, without further purification or working up, as the catalyst for carrying out the reaction according to the invention of aniline and 1-naphthylamine.

If appropriate, the liquid phase comprising the largest part of the organic material is washed once or several further times, with the addition of water and, if appropriate, one or more additional inorganic auxiliaries, and thereafter subjected to working up by distillation. N-Phenyl-1-naphthylamine is obtained in a very pure form in the final working up of the reaction product by distillation. Excess aniline and/or 1-naphthylamine is likewise obtained in a quality such that the two components can be recycled into the preparation process without problems. Small amounts of distillation residues are subject to a residual substance utilization or discarded.

The working up by distillation can be carried out in a manner known per se. A continuous or a discontinuous procedure is possible in principle here. The individual undesirable components, such as, for example, water which remains, excess reactants or by-products, can be separated off, for example, by fractional distillation from a distillation flask or by means of several distillation apparatuses connected in series. In principle, all the distillation apparatuses which are known to the expert and are suitable for the separation task mentioned can be employed here.

The process according to the invention for the preparation of N-phenyl-1-naphthylamine can in principle be carried out in a discontinuous or continuous manner in its entirety or in component areas. Preferably, the actual reaction of aniline with 1-naphthylamine is carried out in a discontinuous manner; the subsequent working up however, can follow in a continuous manner.

The exceptionally high efficiency of the process according to the invention is surprising and has not previously been described in the literature. On the contrary, operations which are more complicated or are significantly more susceptible to interference by side reactions, such as, for example, the alternative processes discussed above, have been proposed.

The reactants aniline and 1-naphthylamine employed for the preparation of N-phenyl-1-naphthylamine are employed in a molar ratio which is 1:3 to 10:1, preferably 1:2 to 5:1, and particularly preferably 1:1 to 3:1. The state of aggregation in which the particular components are introduced into the reaction is unimportant here. In a preferred embodiment, both aniline and 1-naphthylamine are employed in the reaction in liquid form. However, it may also be advantageous, for example, to introduce 1-naphthylamine as a solid or aniline in vaporized form into the reaction mixture.

The catalyst introduced, according to the process according to the invention, into the reaction for the preparation of N-phenyl-1-naphthylamine or the catalyst mixture is employed in an amount such that the molar ratio between the substance amount of boron present in the catalyst or catalyst mixture and the total substance amount of the aniline and 1-naphthylamine employed in the reaction is between 1:10 and 1:100,000, preferably between 1:25 and 1:10,000, and particularly preferably between 1:50 and 1:1,000. The catalyst according to the invention or the catalyst mixture is in general introduced into the reaction mixture in liquid form. In principle, however, it is also possible for the catalyst according to the invention or the catalyst mixture to be introduced into the reaction according to the invention, for the preparation of N-phenyl-1-naphthylamine, in solid form as a catalytically active mixture, after evaporation of catalyst-containing solutions such as are obtained, for example, in the preparation of fresh catalyst batches or in the recovery of catalyst in the course of further working up of reacted reaction mixtures.

The reaction according to the invention for the preparation of N-phenyl-1-naphthylamine is carried out under normal ambient pressure. The reaction according to the invention for the preparation of N-phenyl-1-naphthylamine is carried out in the temperature range between 100 and 400° C., preferably between 150 and 300° C., particularly preferably 180 and 250° C. To ensure the chosen temperature level, the necessary heat energy is fed to the reaction vessel by external and/or internal heating units. A preferred embodiment of the process according to the invention is carried out at the boiling temperature of the reaction mixture established autogenously under the given circumstances, which has a tendency to rise as the conversion progresses due to a decrease in the low-boiling content and an increase in the high-boiling content.

The reaction mixture is mixed thoroughly in the course of the reaction for the preparation of N-phenyl-1-naphthylamine. This can be effected, for example, by stirring units, by external or internal circulatory pumping devices or in another suitable manner. In principle, however, it is also possible to dispense with any active thorough mixing of the reaction mixture in the course of the reaction, since the ammonia gas liberated in the course of the reaction and the boiling of the reaction mixture likewise lead to thorough mixing.

The ammonia gas escaping in the course of the reaction of the reactants is separated off and put to further use or disposal according to regulations. The ammonia gas escaping in the course of reaction of the reactants is in general separated off with the aid of suitable condensers known to the expert for this purpose, the operating conditions of which are chosen such that they allow passage of the ammonia gas but retain the considerably higher-boiling reactants and the reaction products in the reaction region.

In addition to the reaction conditions mentioned and the apparatus parameters, the duration of the reaction according to the invention for the preparation of N-phenyl-1-naphthylamine is decisive for the degree of reaction achieved between the reactants aniline and 1-naphthylamine employed. Since the process according to the invention for the preparation of N-phenyl-1-naphthylamine allows the recycling of unreacted aniline and/or 1-naphthylamine, the reaction time can be varied within wide limits and, for example from process economy aspects, can be chosen such that the space/time yields of the reaction part of the process according to the invention are as high as possible and the expenditure on separation for recycling of unreacted starting material is as low as possible. In general, more than 50%, preferably more than 60%, particularly preferably more than 70%, of the 1-naphthylamine introduced into a discrete reaction batch in the case of a continuous procedure or into the reaction zone in the case of a continuous procedure is reacted.

Water and/or a water-containing solution of recovered catalyst mixture from previous working up operations is added to the reaction mixture obtained after the end of the reaction, preferably after cooling to a temperature below 100° C., and the components are mixed. The two-phase mixture thereby obtained is subjected to phase separation. The amount of water employed in this extraction process and/or of water-containing solution of catalyst mixture recovered from previous working up operations is preferably chosen such that the aqueous extract finally obtained after the phase separation mentioned comprises approx. 10–35% of catalytically active components which cannot be evaporated. The temperature of the two-phase mixture is in general kept in the range between 40 and 100° C. in the course of the extraction and the phase separation.

The organic phase obtained after the phase separation mentioned is preferably subjected to a further extraction. In principle, however, it is also possible to distil it without further treatment. The second extraction is carried out with water to which, where appropriate, between 0 and 50%, preferably between 5 and 30%, particularly preferably between 10 and 20%, of one or more auxiliaries, preferably one or more salt-like inorganic auxiliaries, particularly preferably one or more substances from the group consisting of alkali metal and alkaline earth metal halides, alkali metal sulfates, alkali metal carbonates and alkali metal bicarbonates, has been added. The temperature of the two-phase mixture is in general kept in the range between 30 and 90° C. in the course of the extraction and the phase separation. The two-phase mixture thereby obtained is subjected to phase separation. The aqueous phase obtained after the phase separation mentioned is partly re-used for further extractions and partly sluiced out and fed to a utilization or disposal according to regulations. The organic phase obtained after the phase separation is fed to the separation by distillation. This separation by distillation is preferably carried out, for example with the aid of conventional distillation apparatuses and distillations techniques known to the expert, such that unreacted aniline and 1-naphthylamine present in the crude distillation mixture are recovered completely and can be re-employed in later reactions for the preparation of N-phenyl-1-naphthylamine.

EXAMPLES

Example 1

3.00 kg (6.01 moles) of a 21.0% solution of ammonium tetrafluoroborate in water are added to a mixture of 82.00 kg (880.49 moles) aniline and 72.00kg (502.83 moles) 1-naphthylamine. The mixture was heated at a temperature of approx. 100° C. under a pressure of 20 mbar for approx. 2 hours, approx. 10 kg of a mixture of aniline and water distilling off. A further 10.00 kg (107.38 moles) aniline were added to the reaction mixture and the mixture was now heated at temperatures of between 200 and 215° C. under normal pressure for 24 hours. Boiling aniline was prevented from escaping by a condenser mounted on the vessel, while the ammonia gas formed was removed at the top of the condenser. When the reaction had ended, the reaction mixture was allowed to cool to approx. 100° C. and 17.00 kg of an 18% solution of ammonium tetrafluoroborate in water were added. After intensive thorough mixing at temperatures of between 60 and 80° C., the mixture was allowed to settle. The lower phase was separated off and stored at temperatures above 50° C. It could be re-used as a catalytically active mixture in subsequent reaction batches. 17.00 kg of an approx. 15% solution of sodium carbonate in water were added to the upper phase. After intensive thorough mixing at temperatures of between 60 and 80° C, the mixture was allowed to settle. The lower phase obtained as a result was separated off and discarded. The upper phase obtained was subjected, after its removal, to a fractional distillation under approx. 2 mbar. The following were obtained after complete separation by distillation:

1. 47.75 kg of unreacted aniline which still contained residues of water;
2. 7.35 kg of unreacted 1-naphthylamine, which still contained small amounts of by-products, such as, for example, diphenylamine;
3. 2.89 k(g of crude N-phenyl-1-naphthylamine;
4. 93.37 kg of pure N-phenyl- 1 -naphthylamine, analysis: GC 99.88%, content of 2-naphthylamine <1 ppm;
5. 1.84 kg of distillation residues.

Fractions 1., 2. and 3. could be used as the starting material for further reaction batches. The yield of pure N-phenyl-1-naphthylamine, based on the 1-naphthylamine reacted, was 94.1% of the theoretical yield. Including the crude fraction 3., the yield was 97.0% of the theoretical yield, based on the 1-naphthylamine reacted.

Example 2

Procedure as in example 1, but instead of the aqueous solution of ammonium tetrafluoroborate, approx. 3.5 kg of the aqueous solution which had been separated off as the first lower phase of the reaction mixture in example 1 were used. The yield of pure N-phenyl-1-naphthylamine was 92.9 kg (based on the 1-naphthylamine reacted) =93.6% of the theoretical yield). Including the fractions containing crude N-phenyl-1-naphthylamine, the chemical yield, based on the 1-naphthylamine reacted, was 96.5% of the theoretical yield.

Analysis: GC 99.85%, content of 2-naphthylamine <1 ppm

Example 3
(Preparation of Catalyst Mixture)

50.0 kg (536.9 moles) aniline were initially introduced into a high-grade steel tank and 12.0 kg (194.1 moles) boric acid were added at room temperature in the course of approx. 15 minutes, while stirring. 20.0 kg (729.6 moles) of a 73% aqueous hydrofluoric acid solution were allowed to run in over a period of approx. 120 minutes while stirring and while the temperature of the reaction mixture was kept within a range between 20 and 60° C. by means of external cooling.

Example 4

Procedure as in example 1, but instead of the aqueous solution of ammonium tetrafluoroborate, 3.0 kg in total of the catalyst mixture from example 3 were used. The yield of pure N-phenyl-1-naphthylamine was 93.1 kg (based on the 1-naphthylamine reacted=93.8% of the theoretical yield). Including the fractions containing crude N-phenyl-1-naphthylamine, the chemical yield, based on the 1-naphthylamine reacted, was 96.7% of the theoretical yield.

Analysis: GC 99.87%, content of 2-naphthylamine <1 ppm.

What is claimed is:

1. A process for the preparation of N-phenyl-1-naphthylamine by reaction of aniline and 1-naphthylamine in the liquid phase at 100–400° C. under normal ambient pressure, characterized in that the reaction is carried out in the presence of a catalyst mixture comprising boron and fluorine.

2. The process according to claim 1, characterized in that the reaction is carried out at between 150 and 300° C.

3. The process according to claim 1, characterized in that the reaction is carried out in the presence of a catalyst mixture obtained by reaction of hydrogen fluoride, boric acid and at least one of the compounds selected from aniline and 1-naphthylamine.

4. The process according to claim 1, characterized in that when the reaction of the reactants has ended, the catalytically active components are recovered by extraction of the resulting product mixture.

5. A process according to claim 4, characterized in that the extraction of the resulting product mixture is carried out with water or water-containing solutions of the catalytically active components.

6. A process according to claim 1, characterized in that the reaction is carried out in a discontinuous manner.

7. A process according to claim 6, characterized in that the reaction is carried out in a discontinuous manner but the working up is carried out continuously.

8. The process of claim 1 in which the reaction is conducted at a temperature of from 180 to 250° C.

9. The process of claim 1 in which the catalyst is a mixture of salt-like compounds represented by the formula $$AX \qquad \text{(ii)}$$

A in which

A represents an $H^+$, $NH_4^+$, phenyl-$NH_3^+$, (1-naphthyl)-$NH_3^+$, phenyl-$NH_2$-phenyl$^+$, or phenyl-$NH_2$-(1-naphthyl)$^+$ cation, and X represents an anion corresponding to the formula $$B(OH)_n F_{4-n}^-$$

in which n represents an integer of from 0 to 4.

10. The process of claim 9 in which

A represents an $H^+$, $NH_4^+$, phenyl-$NH_3^+$ or 1-naphthyl-$NH_3^+$ cation and X represents the anion $BF_4^-$.

11. The process of claim 10 which A represents $NH_4^+$ or phenyl-$NH_3^+$.

12. The process of claim 1 in which the catalyst is $NH_4^+BF_4^-$ and/or phenyl-$NH_3^+BF_4^-$.

* * * * *